United States Patent [19]

Sekine et al.

[11] Patent Number: 5,347,328
[45] Date of Patent: Sep. 13, 1994

[54] APPARATUS FOR MEASURING AN INTRAOCULAR LENGTH BETWEEN ANTERIOR AND POSTERIOR PORTIONS OF AN EYE

[75] Inventors: Akihiko Sekine; Funio Ohtomo, both of Tokyo, Japan

[73] Assignee: Kabushiki Kaisha Topcon, Tokyo, Japan

[21] Appl. No.: 872,266

[22] Filed: Apr. 21, 1992

[30] Foreign Application Priority Data

Apr. 22, 1991 [JP] Japan .................................. 3-090878

[51] Int. Cl.$^5$ .............................................. A61B 3/10
[52] U.S. Cl. .................................... 351/211; 351/205; 351/221
[58] Field of Search ............... 351/211, 221, 212, 247, 351/214, 205

[56] References Cited

U.S. PATENT DOCUMENTS

| | | | |
|---|---|---|---|
| 4,796,989 | 1/1989 | Fukuma et al. | 351/212 |
| 4,859,051 | 8/1989 | Fukuma et al. | 351/211 |
| 5,141,302 | 8/1992 | Arai et al. | 351/211 |

Primary Examiner—William L. Sikes
Assistant Examiner—Hung Xuan Dang
Attorney, Agent, or Firm—Finnegan, Henderson Farabow, Garrett & Dunner

[57] ABSTRACT

An apparatus for measuring an eye axial length includes a measuring optical system for projecting laser beam onto an eye and making interference between light reflected by the cornea of the eye and light reflected by the retina of the eye. The measuring optical system includes beam splitting means for splitting the beams of light reflected by the cornea and the retina each into two each for different optical systems, a cornea reflected light receiving optical system for receiving the light reflected by the cornea, a retina reflected light receiving optical system for receiving the light reflected by the retina, and an interference light receiving optical system for reuniting each reflected light at the substantially identical wave front and receiving interference light.

12 Claims, 6 Drawing Sheets

SIGNAL PROCESSING CIRCUIT

APPARATUS FOR MEASURING AN INTRAOCULAR LENGTH BETWEEN ANTERIOR AND POSTERIOR PORTIONS OF AN EYE

BACKGROUND OF THE INVENTION

1. Field of the Invention

This invention relates to an apparatus for measuring an eye axial length wherein interference is made between light reflected by a cornea of an eye to be tested and light reflected by a retina of the eye in order to measuring the length of an eye axis.

2. Description of the Art

Heretofore, there has been an apparatus for measuring an eye axial length as shown in FIG. 6.

In FIG. 6, laser beam emitted from a semiconductor laser 1 is made into a parallel flux of light rays by a collimator lens 2. The parallel flux of light rays are guided to an eye E through an amount of light adjusting filter F and a beam splitter 3. The laser beam is projected onto the retina Er of the eye so as to be converged upon the retina Er by the crystalline lens, e.g., of the eye. And light reflected by the retina Er and light reflected by the cornea Ec, which both have passed through a lens 4, are interfered with each other on a pinhole plate 6. Light interfered thereon is then received by a light receiving element 5 to vary the wavelength of the laser beam. Light receiving signals outputted from the light receiving element 5 are processed by a signal processing circuit 7 and the length of an eye axis (a visual line) between the retina Er and the cornea Ec is measured.

However, in the conventional apparatus for measuring an eye axial length, the light reflected by the cornea Ec becomes scattered light since the parallel flux of light rays are projected onto the cornea Ec. On the other hand, the laser beam is projected onto the retina Er so as to be converged upon the retina Er, as mentioned above, and the reflected light by the retina Er is transformed into a parallel flux of light rays by the refracting function of the crystalline lens or the cornea Ec. Therefore, a difference in wave front between the reflected lights by the retina Er and the cornea Ec is distinctive because one is scattered light and the other one parallel light. That is, there are the drawbacks that a space between the bands of interference fringes is narrow, only a light receiving element with a small area for receiving light must be used, and light receiving signals are weak. In the case of a light receiving element with a large area, a plurality of interference fringes are simultaneously received and light receiving signals corresponding to the interference fringes are averaged in varying wavelengths although the amount of light of the light to be received is increased. This means a similar phenomenon to no fringe after all. Hence, it is impossible to obtain light receiving signals corresponding to interference fringes. Further, owing to a coarse surface of the retina Er, the intensity of interference fringes is so weak that a clear distinction between the light receiving signals of interference fringes obtained by the light receiving element and noises is not easily made.

SUMMARY OF THE INVENTION

An object of the present invention is to provide an apparatus for measuring an eye axial length wherein the wave front of light reflected by the cornea and the wave front of light reflected by the retina can coincide with each other and interference is efficiently made between the two reflected beams of light.

The apparatus is characterized by:

light splitting means for guiding the reflected lights from the cornea and the retina each to an individual optical system;

a light receiving optical system for receiving the reflected light from the cornea split by the splitting means;

a light receiving optical system for receiving the reflected light from the retina split by the splitting means; and an interference light receiving optical system for synthesizing the reflected lights received in each receiving optical system substantially at the same wave front, making interference, and receiving it.

Further, the apparatus is characterized by:

an interference light receiving optical system for receiving interference light;

a cornea illuminating optical system for illuminating the cornea so as to be converged upon the cornea and guiding light reflected by the cornea to the light receiving optical system for the cornea; and a retina illuminating optical system for illuminating the retina so as to be converged upon the retina and guiding light reflected by the retina to the light receiving optical system for the retina; the cornea and retina illuminating optical systems being arranged so that the two reflected beams of light interfere with each other substantially at the same wave front and guiding the interference light to the interference light receiving optical system.

DETAILED DESCRIPTION OF THE EMBODIMENT

The embodiment of an apparatus for measuring an eye axial length according to the present invention will be hereinafter described in relation to the appended drawings.

Figure 1:
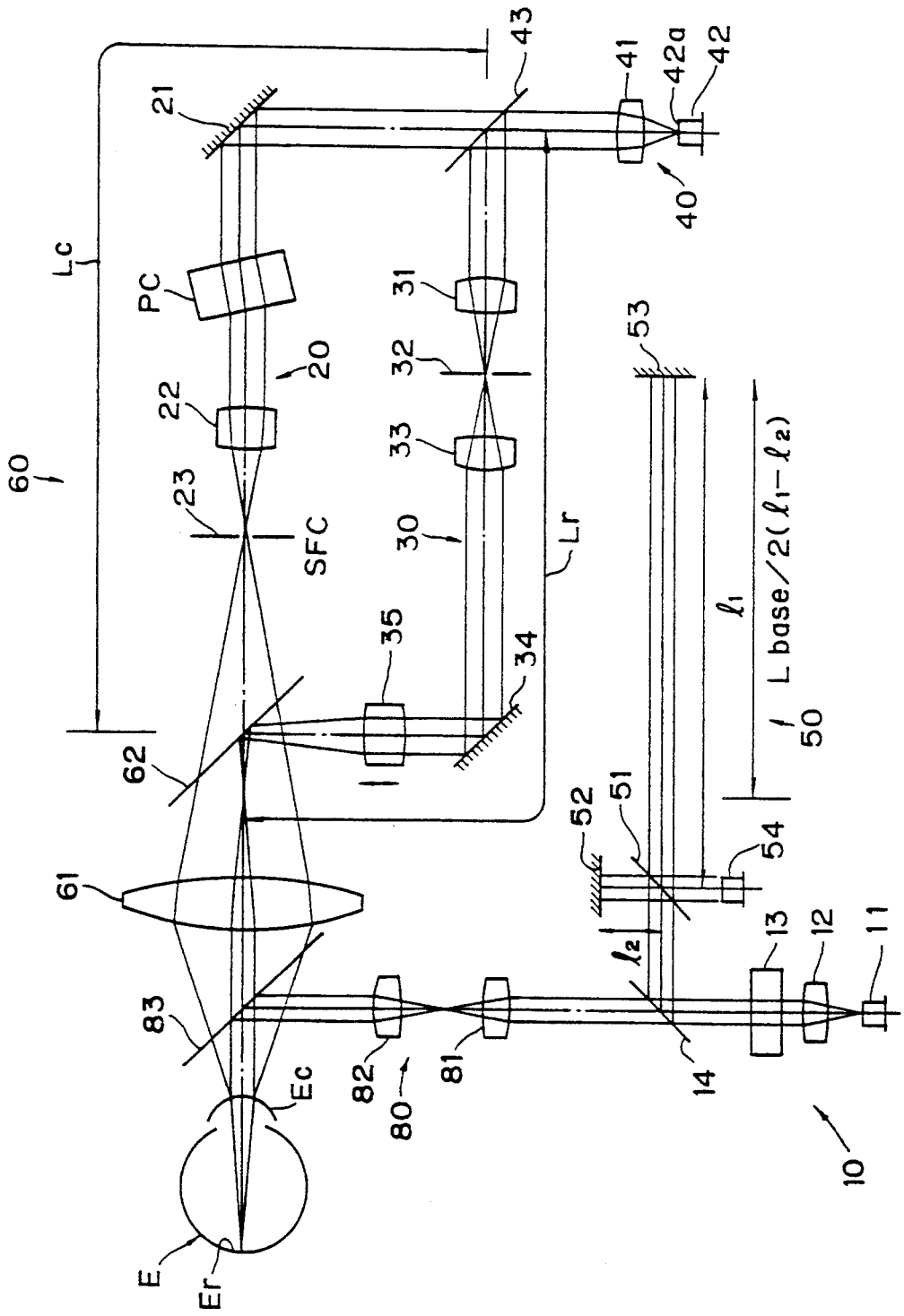
FIG. 1 is a view showing an optical system of a first embodiment of the present invention.

FIG. 1 is an optical system showing the first embodiment of the present invention. The measuring apparatus for measuring an eye axial length (a visual line length) in the first embodiment includes a measuring optical system 10 for emitting laser beam onto an eye E, a measuring interference optical system 60 for guiding light reflected by the eye E to a light receiver 42, and a reference interference optical system 50.

The measuring optical system 10 includes a semiconductor laser (laser source) 11 to omit laser beam, a collimator lens 12 to transform the laser beam into a parallel flux of light rays, a light isolator 13 to prevent reflected light from making incident on the semiconductor laser 11, a beam splitter 14 to split the laser beam into two beams of light and guide one of the beams to the reference interference optical system 50, and a projecting optical system 80 to project the other one of the split beams onto the eye E.

The semiconductor laser 11 is provided with a heating or cooling plate, not shown, which is provided with a Peltier effect type of element, not shown. The control of the Peltier effect type of element results in the control of the chip temperature of the semiconductor laser 11.

The projecting optical system 80 includes a refracting power correcting lens 81 to converge the laser beam upon the retina Er of the eye E, a collimator lens 82, and a beam splitter 83 to split the laser beam. The refracting power correcting lens 81 corrects a refracting power of the eye E by moving it in the direction of the optical axis. The beam splitter 83 reflects the laser beam, which has passed through the collimator lens 82, toward the eye E and transmits the laser beam which has been reflected by the eye E. The reflected light which has passed through the beam splitter 83 makes incident on the measuring interference optical system 60.

The measuring interference optical system 60 includes an objective lens 61 to converge the reflected light from the eye E, a beam splitter 62 to split the reflected light converged by the objective lens 61 into two beams of light, a retina reflected light optical system 30, a cornea reflected light optical system 20, and an interference light receiving optical system 40. The retina reflected light optical system 30 receives the light reflected by the retina by means of the beam splitter 62 and guides it to the interference light receiving optical system 40. The cornea reflected light optical system 20 receives the light reflected by the cornea by means of the beam splitter 62 and guides it to the interference light receiving optical system 40. The interference light receiving optical system 40 makes interference between the reflected beams of light which have passed through the retina and cornea reflected light optical systems 30 and 20 and receives the interference light.

The cornea reflected light optical system 20 includes a total reflection mirror 21, an optical path length compensating plate PC, a lens 22, and a diaphragm 23 to be disposed at the position conjugate with a virtual image formed by the reflected light from the cornea and remove the reflected light except from the cornea.

The optical path length compensating plate PC serves to equalize an optical path length Lr of the retina reflected light optical system 30 with an optical path length Lc of the cornea reflected light optical system 20.

The retina reflected light optical system 30 includes a lens 31, a diaphragm 32 to be disposed at the position conjugate with the retina and remove the reflected light except from the retina, a lens 33, a total reflection mirror 34, and a converging lens 35 to correct the refracting power of the eye E by moving it in the direction of the axis and converge the reflected light from the retina upon the diaphragm 32.

The laser beam in the measuring optical system 10 is reflected by the beam splitter 83 and is projected onto the eye E. Part of the projected laser beam is reflected by the surface of the cornea Ec, and other part reaches the retina Er and is reflected thereby. The reflected light passes through the beam splitter 83 and is guided to the measuring interference optical system 60. And by means of the beam splitter 62, the reflected light is split into a beam of light toward the retina reflected light optical system 30 and a beam of light toward the cornea reflected light optical system 20.

The reflected light made incident on the retina reflected light optical system 30 is converged by the diaphragm 32, the reflected light except from the retina is removed, and it is made into a parallel flux of light rays to make incident on the interference light receiving optical system 40.

On the other hand, the reflected light made incident on the cornea reflected light optical system 20 is converged upon the diaphragm 23 and the reflected light except from cornea is removed. That is, when a virtual image formed by the reflected light from the cornea coincides with the position conjugate with the diaphragm 23, only the components of the reflected light from the cornea can pass through the diaphragm 23. The reflected light which has passed through the diaphragm 23 is made into a parallel flux of light rays to make incident on the interference light receiving optical system 40.

The interference light receiving optical system 40 includes a beam splitter 43 to synthesize the reflected beams of light from the retina and cornea each made incident thereon, an image forming lens 41, and a light receiver 42. The reflected beams of light synthesized by the beam splitter 43 make interference with each other, the interference light is converged upon the light receiver 42, and interference fringes are formed on the surface 42a of the light receiver 42. The light receiver 42 outputs light receiving signals in response to the intensity of the interference fringes.

As mentioned above, the reflected light from the retina reaches the beam splitter 43 in the form of parallel light made by the retina reflected light optical system 30 and the reflected light from the cornea reaches the beam splitter 43 in the form of parallel light made by the cornea reflected light optical system 20, so that the wave fronts of the reflected beams of light from the retina and cornea coincide with each other and each reflected light efficiently interfere with each other.

Therefore, a space between the bands of the interference fringes is in appearance enlarged and the surface 42a of the light receiver 42 is allowed to be enlarged. Since the intensity of the interference light is also increased, the output of the light receiving signals by the light receiver 42 is heightened, hence a clear discrimination between signals and noises is easily carried out.

The reference interference optical system 50 includes beam splitters 14 and 51, total reflection mirrors 52 and 53, and a light receiver 54. In the reference interference optical system 50, laser beams reflected by the total reflection mirrors 52 and 53 are synthesized by the beam splitter 51 to interfere with each other, and the interference light is received by the light receiver 54. A reference optical path difference ($L_a/2$), i.e., a difference between the optical path length from the beam splitter 51 to the total reflection mirror 52 and the optical path length from the beam splitter 51 to the total reflection mirror 53 is arranged sufficiently longer than the eye axial length $L_a$.

While the wavelength of the laser beam is continuously varied, the intensity of light received by the receivers 42 and 54 is varied according to the wavelength, an amount of variation of the wavelength, and an optical path difference between the two beams to be interfered, i.e., a difference between a distance where the reflected light from the cornea Ec travels up to the light receiver 42 and a distance where the reflected light from the retina Er travels through the cornea Ec up to the light receiver 42. Therefore, the eye axial length can be calculated from the variation in intensity represented by light receiving signals.

A phase difference at the light receiver 54 for the initial duration is $2\pi(L_2/\lambda)$ where an optical path difference of the reference interference optical system 50 is $L_2/2$ (constant), an optical path difference as the total of an optical path difference (Lr-Lc) between the retina and cornea reflected light optical systems 30 and 20 and a double optical path difference of the eye axial length (length reduced to air) is $L_3$, the wavelength of the laser beam is $\lambda$, and an amount of variation of the wavelength is $\Delta\lambda$. A phase difference after the variation of the wavelength is $2\pi\{L_2/(\lambda+\Delta\lambda)\}$. While the wavelength is continuously varied, the phase difference is continuously varied from $2\pi(L_2/\lambda)$ to $2\pi\{L_2/(\lambda+\Delta\lambda)\}$. If $\lambda > \Delta\lambda$, the phase difference after the variation of the wavelength is $$2\pi(L_2/\lambda - L_2\Delta\lambda/\lambda^2)$$

Therefore, with the amount of variation of the phase difference $2\pi(L_2\Delta\lambda/\lambda^2)$, the intensity of the interference fringes observed at the light receiver 64 is periodically varied according to the variation of the wavelength.

Also, with the amount of variation of the phase difference $2\pi(L_3\Delta\lambda/\lambda^2)$, the intensity of the interference fringes observed at the light receiver 42 is periodically varied according to the variation of the wavelength. The eye axial length can be calculated based on signals with the periodically variable intensities at the receivers 54 and 42.

If each amount of variation of the phase difference at the light receivers 42 and 54 is represented by $\phi 1$ and $\phi 2$, namely $$\phi 1 = 2\pi(L_3\Delta\lambda/\lambda^2) \quad (1)$$

$$\phi 2 = 2\pi(L_2\Delta\lambda/\lambda^2) \quad (2)$$

the following equation is obtained.

$$2L_3 = L_2 \cdot \phi 1/(\phi 2) \quad (3)$$

Therefore, $2L_3$ can be found according to each amount of variation of the phase difference of the signals obtained at the receivers 42 and 54. By subtracting an optical path difference $L_3 = Lr - Lc$ between the retina and cornea reflected light optical systems 30 and 20 from the obtained value $2L_3$, the double value $2L_1$ of the length $L_1$ in terms of air can be obtained. And by dividing the value $L_1$ by a refractive index n inside the eyeball (the index n is an average value based on the configuration or composition of the eyeball), the eye axial length AL can be found. Namely, $$AL = L_1/n \quad (4)$$

The variation of wavelengths and the process of signals will be now described hereinafter.

Figure 3:
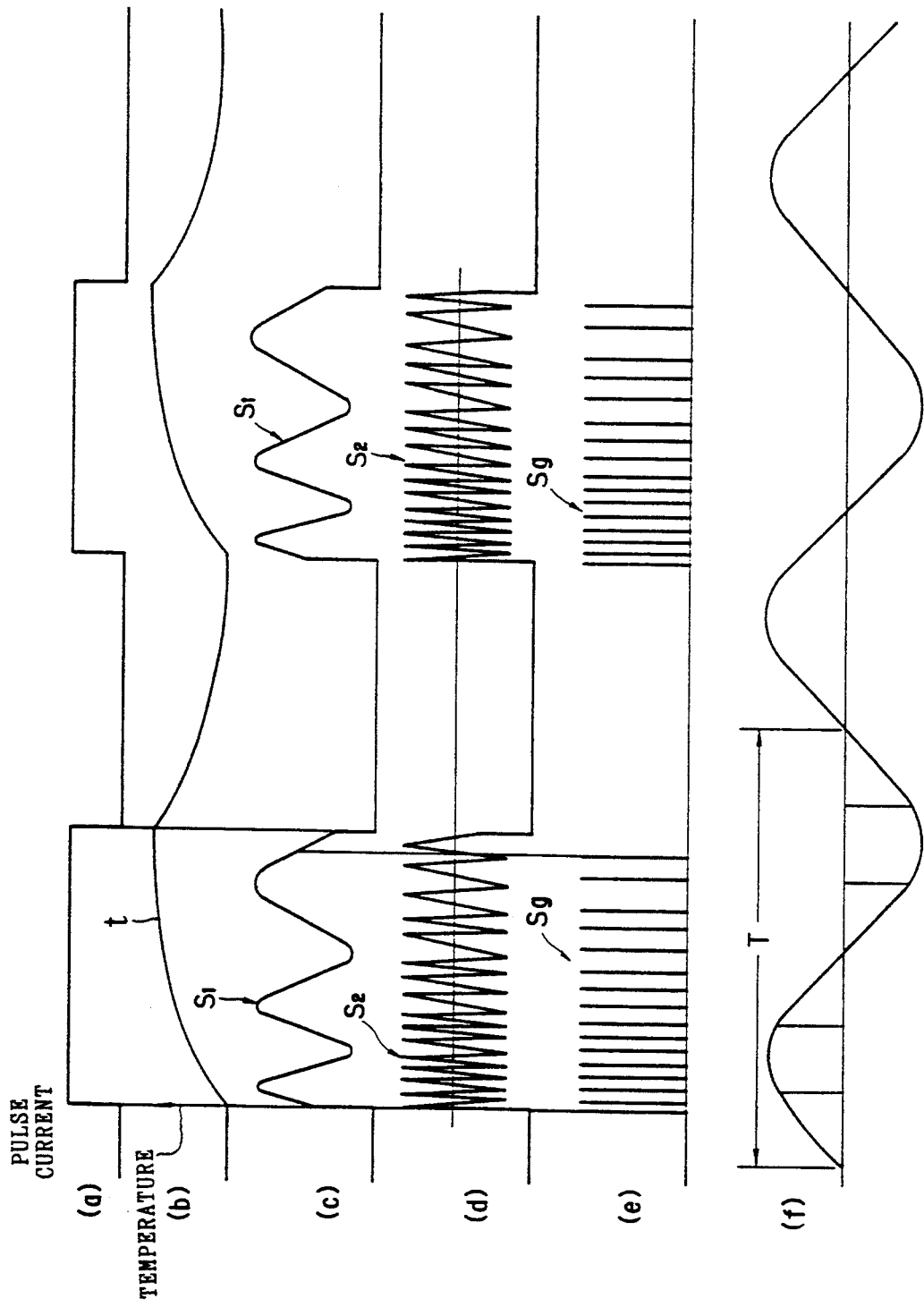
FIG. 3 shows signals outputted by each circuit of the signal processing circuit.

The semiconductor laser 11 is pulsationally driven by rectangular wave signals (see (a) of FIG. 3), thereby the chip temperature of the semiconductor laser 11 is increased, and a certain amount of time is taken to equilibrate the chip temperature. According to the chip temperature of the laser 11 varied is the oscillation wavelength which corresponds to the chip temperature in the ratio of 1 to 1 except the point where a mode hop (mode jump) occurs. That is, when the laser is turned on, the chip temperature thereof begins to vary and incidentally the wavelength of the laser beam begins to vary.

As shown in (b) of FIG. 3, the variation in temperature is most considerable at the beginning of the oscillation and it gradually calms down. After a certain amount of time, the laser 11 is turned off to regain the former temperature and it stops projecting the laser beam. By driving pulsationally the semiconductor laser 11, it is permitted to lessen the average amount of light of the projection light and thereby increase the amount of light thereof when measured. A pulse width is determined based on the width of the variation in wavelength. For example, by rectangularly driving the laser 11 at a speed of 1 KHz or so, principal variation portions of the wavelength in response to the temperature variation is allowed to be used and reproduced.

Figure 2:
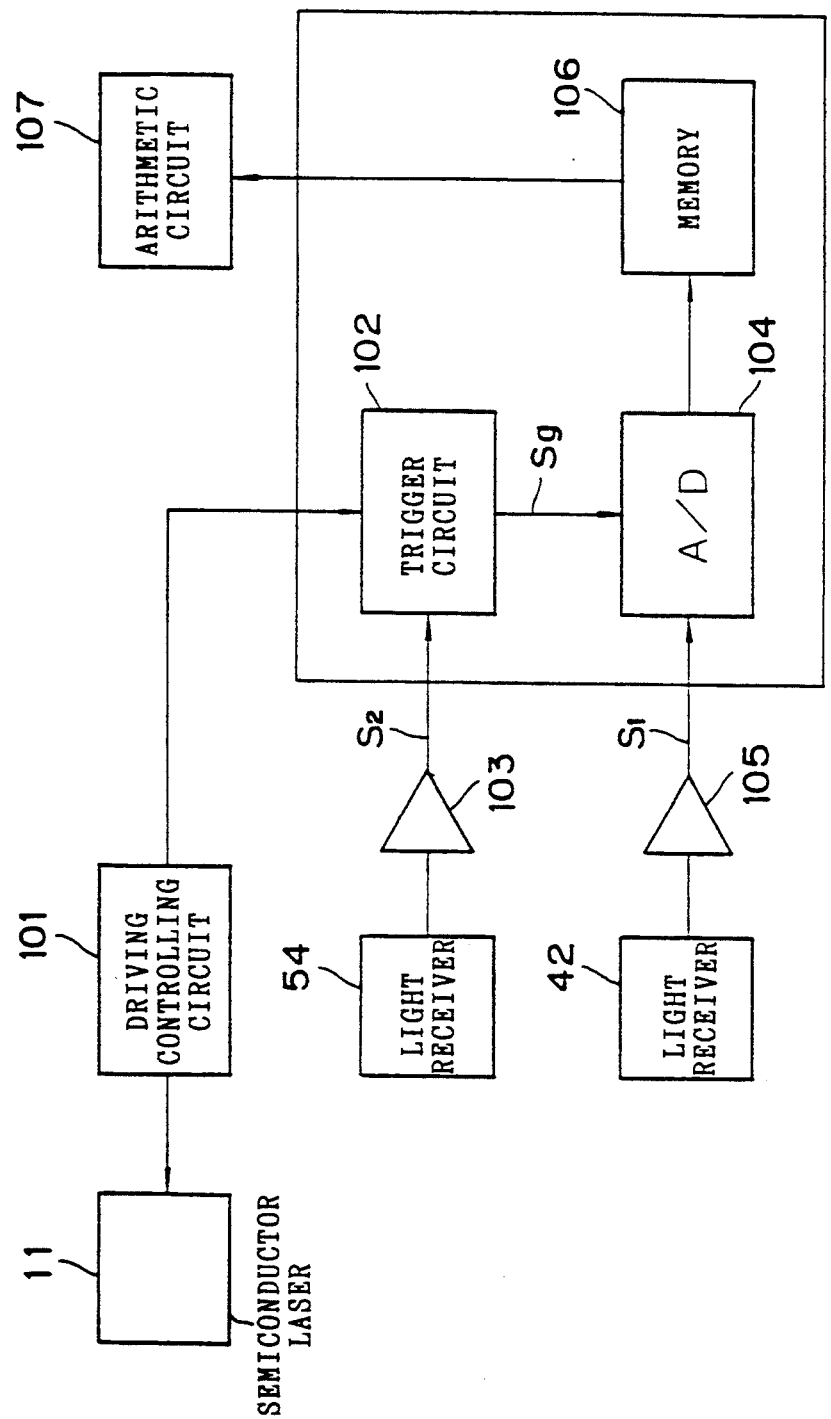
FIG. 2 is a block diagram showing a signal processing circuit for measuring an eye axial length based on light receiving signals outputted by each light receiver.

The semiconductor laser 11 of which the space of the mode hop is wider than the width of the wavelength variation is used. To prevent the mode hop from occurring during the temperature variation for the pulse duration, a reference temperature of the laser, i.e., the wavelength of the laser beam is controlled by a Peltier element, not shown, of a drive controlling circuit 101 as shown in FIG. 2.

In comparison with the temperature variation, the oscillation output variation clams down very quickly, hence supposedly the intensity variation for the pulse duration scarcely occurs. An output variation portion equivalent to a transient duration for which an output becomes stable after applying and switching on a rectangular input is omitted in (a) of FIG. 3. In actual use, it is used just after the transient duration. However, since the wavelength variation is so unlinear as to be sudden at the beginning and decrease gradually, the frequency of signals to be obtained is very high at the beginning and gradually becomes low.

As shown in (c) and (d) of FIG. 3, the frequencies of light receiving signals S1 and S2 outputted from the light receivers 42 and 54 respectively are also high for an initial duration and gradually turns low. If the signals S1 and S2 are transferred from analogue to digital by a trigger with a constant frequency to obtain data without processing the signals, they are stored each as a signal wherein the frequency is high for the initial duration and gradually turns low. Therefore, the data cannot lead to an accurate period of each signal.

According to Eq. (3), the following equation is obtained.

$$2L_3/L_2 = \phi 1/(\phi 2) \quad (5)$$

This means that the ratio of the variation of phase difference between the reference optical path and the measuring optical path directly shows the ratio of the optical path difference. That is, the ratio in phase variation corresponds with the ratio in optical path difference at the identical time and point when the signals of the reference optical system and the measuring optical system are compared with each other in varying the wavelength by a certain amount of variation. This principle can be applied to any cases if the wavelength is successive. Therefore, to obtain signals with an identical period in appearance, the optical path difference of the reference optical path is arranged sufficiently longer than that of the measuring optical path, interference signals from the reference optical system are transformed into trigger signals, interference signals of the measuring optical path are sampled, and the sampled data are arranged in order.

The steps that a trigger signal is generated every one cycle of the interference signal from the reference optical system, measuring signals are sampled based on the trigger signal, and they are stored in a memory mean that triggers with unstable periods are replaced by memory addresses with a same space. Since the ratio of the period of the measuring signal to the trigger period is constant, signals of the memory each have the same period. That is, signals every each pulse are stored in the memory.

Regarding analysis of periods based on the data in the memory, random noises of a plurality of pulses such as 128 pulses are removed on average to analyze the period because actual signals include electrical noises.

Since the period T obtained here is equal to the ratio of the signal to the trigger, i.e., $T=\phi 1/(\phi 2)$, the value $L_s$ is found according to Eq. (6). In actual measurement, signals of light reflected by different surfaces inside the eyeball are removed when analyzed.

FIG. 2 is a block diagram showing a signal processing circuit for measuring the eye axial length $L_1$ according to the above process.

The arrangement and functions of the signal processing circuit will be hereinafter described in relation to the waveforms of FIG. 3.

In FIG. 2, the numeral 101 denotes a drive controlling circuit for driving the semiconductor laser 11 by supplying pulse electric current (see (a) of FIG. 3) to the laser 11. The drive controlling circuit 101 also controls the chip temperature of the laser 11 by means of a Peltier effect type of element not shown. As shown in (e) of FIG. 3, a trigger circuit 102 outputs a trigger signal Sg every one period of a light receiving signal S2 outputted by the light receiver 54 via an amplifier 103. An A/D converter 104 A/D-converts (converts from analogue to digital) a light receiving signal S1 outputted by the light receiver 42 via an amplifier 105 synchronizing with the output of the trigger signal Sg. The numeral 106 denotes a memory for storing digital values converted by the A/D converter 104. The memory 106 stores digital values in response to amplitude values of the signal S1, as shown in (f) of FIG. 3.

An arithmetic circuit 107 calculates the period T based on the data stored in the memory 106. The eye axial length AL is then calculated from the period T according to EQs. (4) and (5).

There has been hereinbefore explained the case where the reflected light from the cornea passes through only the cornea reflected light optical system 20 and the reflected light from the retina passes through only the retina reflected light optical system 30. However, part of the reflected light from the retina which travels near the optical axis of the cornea reflected light optical system 20 may reach the light receiver 42 through the diaphragm 23 (this part of the reflected light will be hereinafter referred to as R3). Similarly, part of the reflected light from the cornea which travels near the optical axis of the retina reflected light optical system 20 may reach the light receiver 42 through the diaphragm 32 (this part as R4). These reflected lights R3 and R4 each interfere with the normal reflected lights, so that interference signals corresponding to phase differences (optical path differences) every each combination of the reflected lights are generated and noises are included in the signals.

This case makes a correction in Eqs. (3) and (4) impossible. To prevent the occurrence of the needless interference signals, the optical path length compensating plate PC is interposed in the the cornea reflected light optical system 20 so that the optical path length of the cornea reflected light optical system 20 is equalized with that of the retina reflected light optical system 30 in this embodiment.

That is, the optical path length between the beam splitters 62 and 43 is equalized (Lr=Lc). By this arrangement moved are a phase difference between the normal reflected light R5 from the retina which has passed through the retina reflected light optical system 30 and the reflected light from the retina R3 which has passed through the cornea reflected light optical system 20, and a phase difference between the normal reflected light R6 from the cornea which has passed through the cornea reflected light optical system 20 and the reflected light from the cornea R4 which has passed through the retina reflected light optical system 30 (the projected beams of light can reach the cornea with the identical wave front).

Since the reflected light received by the light receiver 42 has a phase difference as a difference between an optical length from the receiver 42 to the retina and an optical length from the receiver 42 to the cornea. the signals outputted by the receiver 42 have both interference components during the wavelength variation and components in relation to the above phase difference. If a difference between Lr and Lc is sufficiently smaller than the value $2L_1$ and substantially similar to the wavelength, signals generated by the interference between R3 and R5 and signals generated by the interferance between R4 and R6 cannot occur as a periodic signal.

An amount of variation of the phase difference by the interference between the reflected lights from the retina and cornea is represented by omitting the constant $2\pi \cdot \Delta\lambda/\lambda^2$, as follows:

$$2L_1 = 2L_1 + Ls = 2L_1 - Ls$$

Therefore, it is not influential in moasurement. (Note: according to the principle, the amount of variation of the phase difference $\phi$ in varying the wavelength by $\Delta\lambda$ is represented as $\phi = 2\pi \cdot (2\Delta L \cdot \Delta\lambda)/\lambda^2$ where $\Delta L$ is a optical path difference. If $\Delta L$ is a range of several $\lambda$ to ten times of several $\lambda$, it is not detected as a periodic signal because $\Delta \lambda$ is so small. And it is sufficiently smaller than the period of the interference signal.)

In the above embodiment, refraction power correcting lenses 81 and 35 are individually adjusted independently of each other. However, an arrangement whereby these lenses 81 and 35 are adjusted dependently on each other may be made to simplify the measurement.

Figure 4:
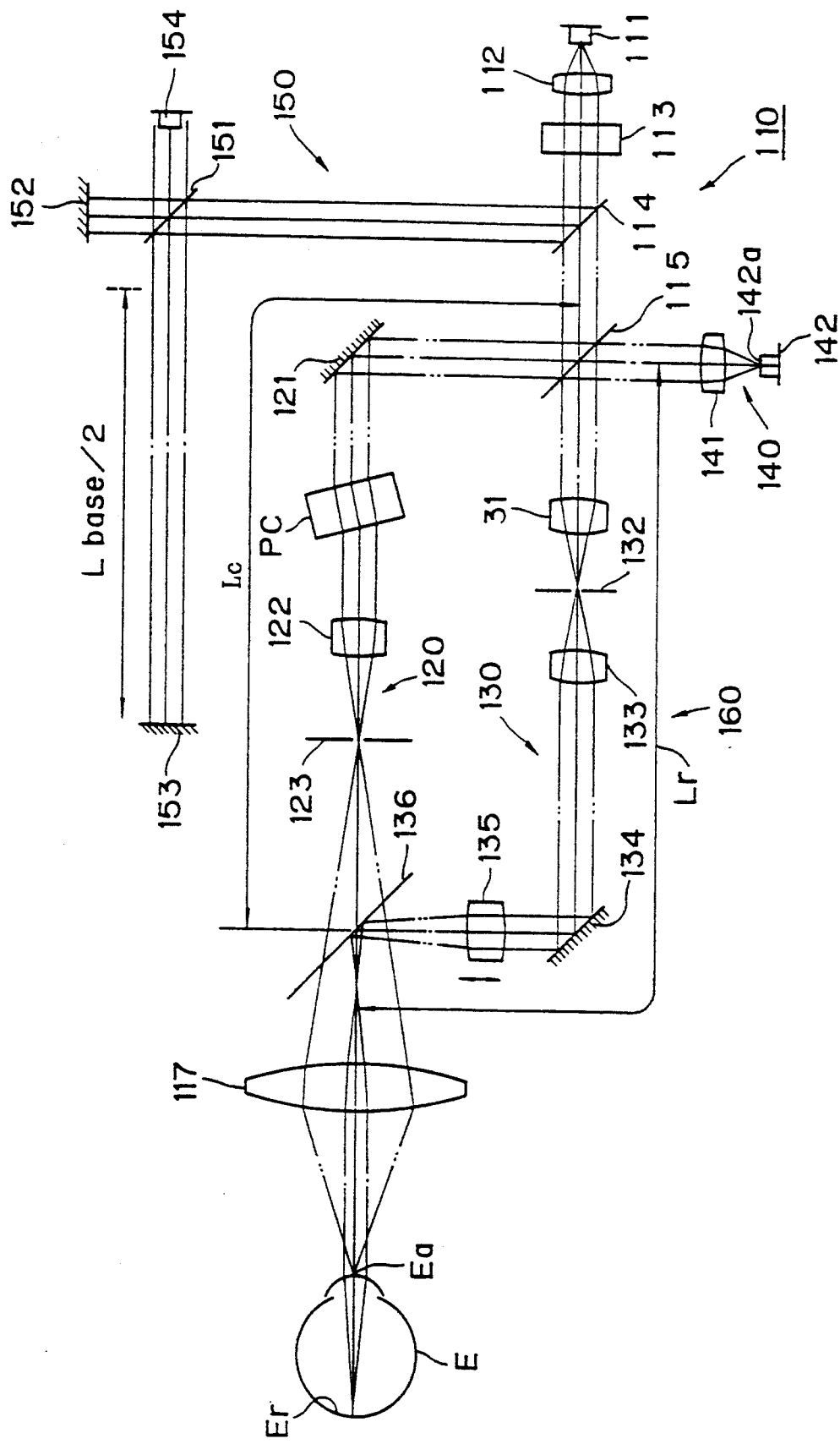
FIG. 4 is a view showing an optical system of a second embodiment of the present invention.

FIG. 4 shows an optical system of a second embodiment of the present invention. In the second embodiment, the optical system for projecting a laser beam onto the eye E and the optical system for receiving the reflected light from the eye E. which are arranged independent of each other in the first embodiment, are shared with each other. A measuring principle, wavelength variation, and signal processing are carried out the same as in the first embodiment.

The measuring apparatus as shown in FIG. 4 includes a measuring optical system 110 to emit a laser beam onto the eye E and a reference interference optical system 150.

The measuring optical system 110 includes a semiconductor laser (laser source) 111, a collimator lens 112 to make the laser beam into parallel flux of light rays, a light isolator 113 to prevent light reflected by the eye from being guided to the laser 111, a beam splitter 114 to split the laser beam into two beams of light and guide either of the two beams to the reference interference optical system 150, and a measuring interference optical system 160 to project the other one of the two beams onto the eye E.

The measuring interference optical system 160 includes a beam splitter 115 to split the beam guided to the reference interference optical system 150 into two beams of light for illuminating the cornea and the retina, a cornea illuminating optical system 120 to illuminate the cornea so as to be converged upon the apex Ea of the eye E through an objective lens 117, a retina illuminating optical system 130 to illuminate the retina so as to be converged upon the retina Er of the eye E through an objective lens 117, and a light receiving optical system 140 to receive interference light made between light reflected by the retina Er and light reflected by the cornea Ea.

The laser 111 is provided with a heating or cooling plate, not shown, which is provided with a Peltier effect type of element, not shown. The chip temperature of the laser 111 is controlled by the Peltier effect type of element.

The cornea illuminating optical system 120 includes a total reflecting mirror 121, an optical path length compensating plate PC, a lens 122, and a diaphragm 123 to be disposed at a position conjugated with the apex of the cornea and remove the reflected light except the light reflected by the cornea.

The retina illuminating optical system 130 includes a lens 131, a diaphragm 132 to be disposed at a position conjugated with the retina Er and remove the reflected light except the light reflected by the retina, a lens 133, a total reflecting mirror 134, a converging lens 135 to correct the refracting power of the eye by moving in the direction of the optical axis, and a beam splitter 136 to synthesizing the laser beams of the cornea and retina illuminating optical systems 120 and 130 and project the synthesized beams of light onto the eye E along an identical optical path.

The optical path length compensating plate PC serves to equalize an optical path length Lc of the cornea illuminating optical system 120 with an optical path length Lr of the retina illuminating optical system 130.

The laser beam for the cornea split by the beam splitter 115 is converged upon around the apex of the cornea, it is reflected thereby, and it is returned through the same system 120. When the convergent point coincides with the apex, the reflected light which has passed the diaphragm 123 is made into a parallel flux of light rays (parallel light) and reaches the beam splitter 115. On the other hand, the laser beam for the retina split by the beam splitter 115 is converged upon the retina Er, it is reflected thereby, and it is returned through the same system 130. The reflected light made into parallel light reaches the beam splitter 115. Each reflected light from the cornea and the retina is interfered with each other at the beam splitter 115 and then the interference light is guided to the light receiving optical system 140.

The light receiving optical system 140 includes an image forming lens 141, and a light receiver 142. The interference light made at the beam splitter 115 is converged upon the surface 142a of the receiver 142 by the image forming lens 141, so that interference fringes are formed on the surface 142a. The light receiver 142 outputs signals in response with the intensity of the interference fringes. The light receiving optical system 140 and the beam splitter 115 compose an interference optical system.

Since each reflected light from the cornea and the retina reaches the beam splitter 115 so as explained above, the wave front of each reflected light coincides with each other, hence they can interfere with each other efficiently.

Therefore, since a space between the bends of the interference fringes formed on the surface 142a is relatively wide, the area of the surface 142a is allowed to be enlarged. Also, since the intensity of the interference light is relatively high, strong signals are outputted by the light receiver 142, hence a clear distinction is made between signals and noises.

The reference interference optical system 150 is arranged the same as in the first embodiment. According to the same principle as in the first embodiment, the wavelength of the laser beam is continuously varied by similar means to those in the first embodiment, and signals are processed to find the eye axial length AL. However, in the second embodiment, the optical path difference $L_3$ of the eye axial length in terms of air is equal to a difference between the length from the retina Er to the beam splitter 115 and the length from the cornea Ec to the beam splitter 115 because the beam of light goes forth and back along the same optical system. That is, the value of the eye axial length in terms of air and an optical path difference between the retina and cornea illuminating optical systems 130 and 120 make the value $L_3$. Therefore, the equation (3) is transformed as follows:

$$L_3 = L_2 \cdot \phi_1 / (2 \cdot \phi_2) \qquad \ldots (3)'$$

Therefore, the eye axial length in terms of air (Leye) is found by subtracting an optical path difference $L_3$ between the retina and cornea illuminating optical systems 130 and 120 from the obtained value $L_3$.

As mentioned above, the light reflected by the cornea passes through only the cornea illuminating optical system 120 and the light reflected by the retina only the retina illuminating optical system 130. However, such reflected light as explained below may trespass on each optical system. For example, part of the laser beam for illuminating the retina is reflected by the cornea, the light reflected by the cornea which travels near the optical path is returned through the cornea illuminating optical system 120, and it reaches the light receiver 142 (this reflected light is referred to as R1). Similarly, part of the laser beam for illuminating the cornea, which travels near the optical path, reaches the retina and is reflected thereby. The reflected light is then returned through the retina illuminating optical system 180 and reaches the light receiver (this reflected light as R2). Also, part of the reflected light from the retina reaches the light receiver 142 through the cornea illuminating optical system 120 (this reflected light as R3). And part of the reflected light from the cornea reaches the light receiver 142 through the retina illuminating optical system 130 (this reflected light as R4). Presumably, the reflected light R1 has a large amount of light, hence they interfere with each other. Therefore, interference signals are produced in response to the phase difference (optical path difference) every each combination of the reflected lights, hence noises are intermingled with the normal signal in varying the wavelength.

To prevent interference signals caused by such needless reflected light from occurring, the optical path length of the cornea illuminating optical system 120 is arranged to be equal to the optical path length of the retina illuminating optical system 130 by interposing the optical path length compensating plate PC in the cornea illuminating optical system 120 in the second embodiment.

In other words, the phases of the laser beams passing through the retina and cornea illuminating optical systems 130 and 120 are arranged to coincide with each other at the apex of the cornea, i.e., each optical path length between the beam splitters 115 and 136 is arranged to be equal to each other (Ln=Lr).

Therefore, the phase difference between the reflected light from the retina (referred to as R5) passing through the retina illuminating optical system 130 and the reflected light R2, the phase difference between R2 and R3, and the phase difference between R5 and R3 are removed. Further, the phase difference between the reflected light from the cornea (referred to as R6) passing through the cornea illuminating optical system 120 and the reflected light R1, the phase difference between R1 and R4, and the phase difference between R6 and R4 are removed. That is, both each phase difference produced among the reflected lights from the retina R2, R3 and R5 and each phase difference produced among the reflected lights from the cornea R1, R4, and R6 results in zero.

Since the phase difference of the reflected light from the eye E is equal to a difference ($L_1 \times 2$) between the optical distance from the light receiver 142 to the retina and the optical distance from the light receiver 142 to the cornea, the interference signal in varying the wavelength can be made into a signal in response to the phase difference ($L_1 \times 2$). Such an optical path difference as in the first embodiment does not necessarily need the identical length of Lo with Lr because of the same reason.

The cornea illuminating light may be adjusted so as to be converged upon the cornea by moving the lens 122 and the diaphragm 128, which are both fixed to the optical axis in the second embodiment, in the direction of the optical axis.

When the cornea illuminating light is converged upon the center of curvature of the cornea regarded as spherical, the reflected light from the center also passes through the diaphragm 123 although the cornea illuminating light passing through the cornea illuminating optical system 120 is converged upon the apex Ea of the cornea in the second embodiment. Since the cornea illuminating light is most reflected by the surface of the cornea, i.e., the difference of refractive indices is largest at the surface of the cornea, the eye axial length can be measured by converging the cornea illuminating light upon the center of the curvature the same as in the above embodiment.

In the second embodiment, when a virtual image formed by the light reflected by the cornea of the retina illuminating light is conjugate with the diaphragm 123, the reflected light passes through the diaphragm 123 and reaches the light receiver 142. Although the phase of the foregoing reflected light is generally different from that of the light reflected by the cornea of the cornea illuminating light, the eye axial length can be measured using the foregoing reflected light by equalizing the optical path length of the cornea illuminating optical system with that of the retina illuminating optical system as shown in the second embodiment because of the same function as in the first embodiment.

Figure 5:
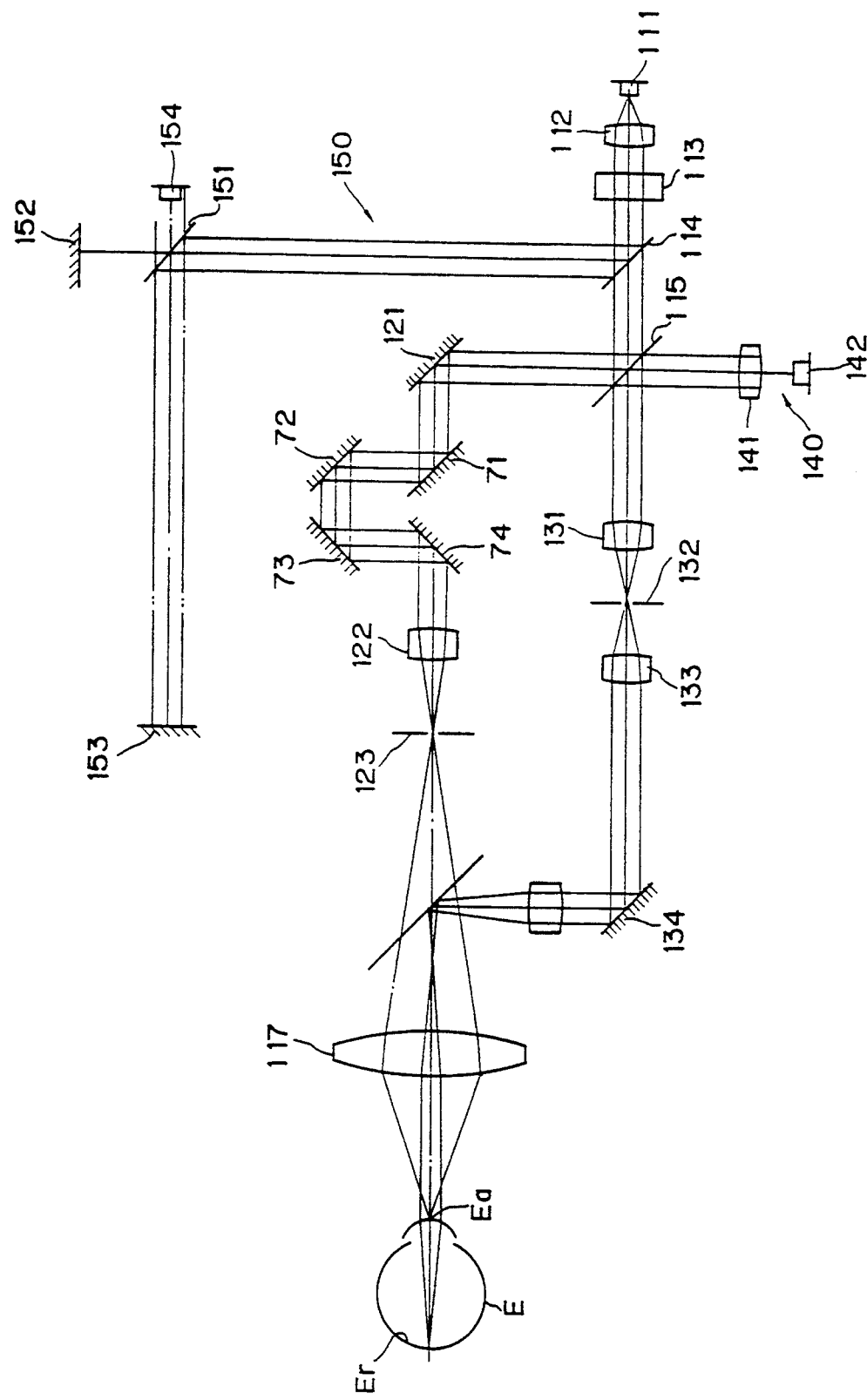
FIG. 5 is a view showing an optical system of a third embodiment of the present invention.
Figure 6:
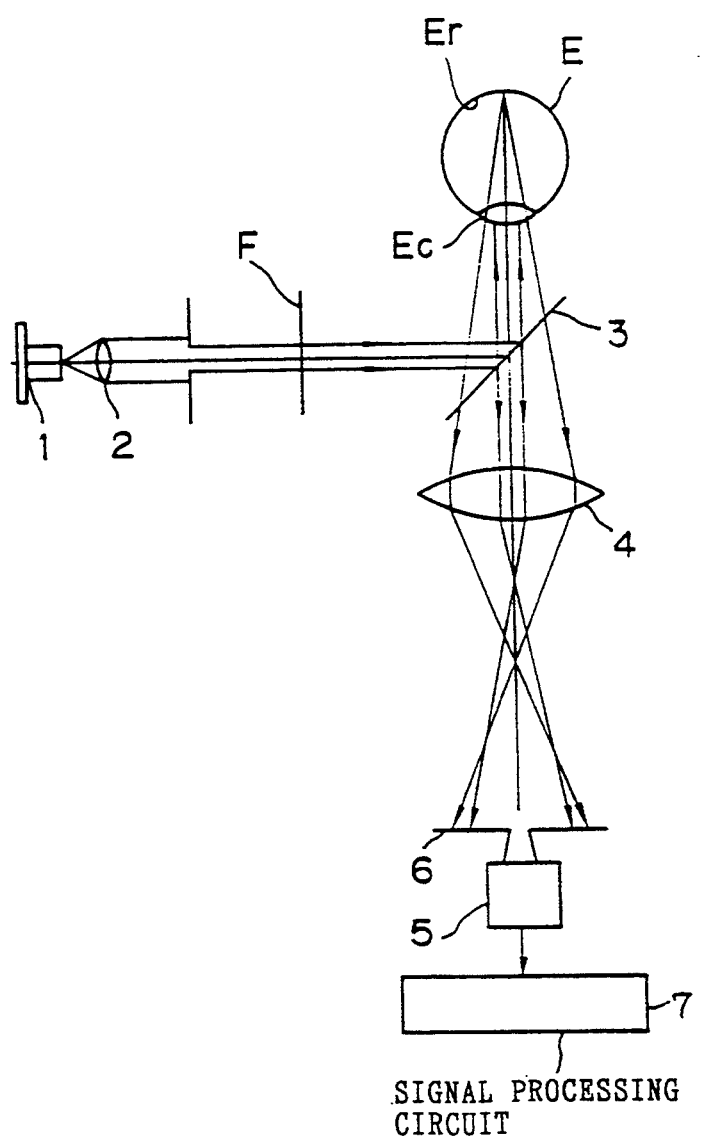
FIG. 6 is a view showing an optical system of a conventional apparatus.

As shown in FIG. 5, total reflecting mirrors 71 to 74 for detouring the optical path may be disposed in place of the optical path length compensating plate PC as shown in FIG. 4. Since the optical path length is adjusted by moving the mirrors 72 and 73, the measuring apparatus is easily and economically manufactured. Also, to compensate the optical path length, the total reflecting mirrors 71 to 74 may be used in place of the optical path length compensating plate PC as shown in FIG. 1.

The beam splitters 115 and 136 as shown in FIG. 4 are each of a normal type. Therefore, the reflected light from the eye E split by the beam splitters 115 and 136 makes a loss in amount of light when it reaches the light receiver 142. To prevent the loss used are a linearly polarized beam of light for illuminating the eye, a polarized beam splitter in place of the beam splitter 136, and a $\lambda/2$ plate disposed in either of the cornea and retina illuminating optical systems in order to obtain an emergent polarized beam of light rotated by 80° with respect to an incident polarized beam of light. If the beam splitter 136 splits the reflected light in the ratio of 50:50, the amount of light of the reflected light at the light receiver 142 is 25% ($0.5 \times 0.5 = 0.25$) in FIG. 1. In the case of the polarized beam splitter, the amount of light is 50% if the reflected light maintains the polarization. The retina does not completely maintain the polarization because of the coarse surface. The reflected light which has passed through the $\lambda/2$ plate regains the former polarization. Although an individual diaphragm is used for the reflected lights from the retina and cornea in the above embodiment, a common diaphragm for the two reflected lights may be disposed at the point simultaneously converging the reflected lights from the retina and cornea by means of the coverging lens of the light receiving optical system. Further, if a light receiver of which a light receiving area is small is disposed at the converging point, the light receiver can serve as a diaphragm, hence the diaphragm needs not be disposed in the optical path. Although the incident light upon the light receiving optical system is not a parallel flux of light rays owing to no diaphragm, the light receiver can select only the components of parallel light.

Further, small mirrors in place of the beam splitters 62 and 136 may be disposed to reflect the light from the retina and transmit the light from the cornea from around the mirrors, so that at least the reflected light from the retina is not guided to the cornea illuminating optical system. Obviously, the mirrors may be of an aperture type or be displaced to exchange the light reflected by the mirrors for the light transmitted thereby.

What is claimed is:

1. An apparatus for measuring an intraocular length between anterior and posterior positions of a living eye, comprising:
   a laser source to emit a laser beam of light, having variable wavelengths, onto said eye; and
   means for measuring interference between light reflected by the anterior portion of said eye and light reflected by the posterior portion of said eye,
   the intraocular length of said eye being measured according to said interference,
   said measuring interference means comprising:

light splitting means for separating said light reflected by the anterior portion and said light reflected by the posterior portion;

an anterior portion reflected light optical system for receiving said light reflected by the anterior portion from said light splitting means;

a posterior portion reflected light optical system for receiving said light reflected by the posterior portion from said light splitting means; and interference light receiving optical system for combining an output from said anterior portion reflected light optical system with an output from said posterior portion reflected light optical system at a substantially identical wave front to produce and receive interference light for measurement.

2. An apparatus for measuring an intraocular length between anterior and posterior portions of a living eye according to claim 1, wherein said anterior portion is a cornea and said posterior portion is a retina.

3. An apparatus for measuring an intraocular length between anterior and posterior portions of a living eye according to claim 2, further comprising optical path length correcting means for equalizing an optical path length of said anterior portion reflected light optical system with an optical path length of said posterior portion reflected light optical system, said optical path length correcting means disposed in at least one of said anterior portion reflected light optical system and said posterior portion reflected light optical system.

4. An apparatus for measuring an intraocular length between anterior and posterior portions of a living eye according to claim 3, wherein said optical path length correcting means comprises an optical path length compensating plate.

5. An apparatus for measuring an intraocular length between anterior and posterior portions of a living eye according to claim 3, wherein said optical path length correcting means comprises a movable reflecting mirror.

6. An apparatus for measuring an intraocular length between anterior and posterior portions of living eye according to claim 2, wherein said anterior portion reflected light optical system includes anterior portion reflected light selecting means for selecting only light reflected by the anterior portion and said posterior portion reflected light optical system includes posterior portion reflected light selecting means for selecting only light reflected by the posterior portion.

7. An apparatus for measuring an intraocular length between anterior and posterior portions of living eye, comprising:

a laser source to emit a laser beam of light, having variable wavelengths, onto said eye; and means for measuring interference between light reflected by said anterior portion of said eye and light reflected by said posterior portion of said eye, the intraocular length being measured according to said interference, said measuring interference means comprising:

a light receiving optical system for receiving interference light;

an anterior portion illuminating optical system for projecting said laser beam of light onto the anterior portion and guiding light reflected by the anterior portion to said light receiving optical system; and a posterior portion illuminating optical system for projecting said laser beam of light onto the posterior portion and guiding light reflected by the posterior portion to said light receiving optical system;

said anterior portion illuminating optical system and said posterior portion illuminating optical system being arranged so that the reflected light from the anterior and posterior portions interferes with each other at a substantially identical wave front and is guided to said light receiving optical system.

8. An apparatus for measuring an intraocular length between anterior and posterior portions of a living eye according to claim 7, wherein said anterior portion is a cornea and said posterior portion is a retina.

9. An apparatus for measuring an intraocular length between anterior and posterior portions of a living eye according to claim 8, further comprising optical path length correcting means for equalizing an optical path length of said anterior portion illuminating optical system with an optical path length of said posterior portion illuminating optical system, said optical path length correcting means disposed in at least one of said anterior portion illuminating optical system and said posterior portion illuminating optical system.

10. An apparatus for measuring an intraocular length between anterior and posterior portions of a living eye according to claim 9, wherein said optical path length correcting means comprises an optical path length compensating plate.

11. An apparatus for measuring an intraocular length between anterior and posterior portions of a living eye according to claim 9, wherein said optical path length correcting means comprises a movable reflecting mirror.

12. An apparatus for measuring an intraocular length between anterior and posterior portions of a living eye according to claim 8, wherein said anterior portion illuminating optical system includes anterior portion reflected light selecting means for selecting only light reflected by the anterior portion and said posterior portion illuminating optical system includes posterior portion reflected light selecting means for selecting only light reflected by the posterior portion.

* * * * *

UNITED STATES PATENT AND TRADEMARK OFFICE
CERTIFICATE OF CORRECTION

PATENT NO. : 5,347,328
DATED : September 13, 1994
INVENTOR(S) : Akihiko SEKINE et al.

It is certified that error appears in the above-indentified patent and that said Letters Patent is hereby corrected as shown below:

Title page, column 1, the second inventor's name, "Funio Ohtomo", is incorrect; the name should read --Fumio Ohtomo--.

Signed and Sealed this

Eleventh Day of April, 1995

*Attest:*

BRUCE LEHMAN

*Attesting Officer*  *Commissioner of Patents and Trademarks*